(12) United States Patent
Snyder et al.

(10) Patent No.: US 11,135,025 B2
(45) Date of Patent: Oct. 5, 2021

(54) SYSTEM AND METHOD FOR REGISTRATION BETWEEN COORDINATE SYSTEMS AND NAVIGATION

(71) Applicant: Medtronic Navigation, Inc., Louisville, CO (US)

(72) Inventors: Victor D. Snyder, Erie, CO (US); Matthew F. Dicorleto, Boulder, CO (US); Joseph Moctezuma, Golden, CO (US); David E. Macht, Littleton, CO (US); Jeremiah R. Beers, Westminster, CO (US); Katherine M. Puckett, Denver, CO (US); Katharine E. Darling, Arvada, CO (US); Leonid Kleyman, Atzmon-Segev (IL); Dany Junio, Tel Aviv (IL); Dana Gazit-Ankori, Zichron Yaakov (IL); Eliyahu Zehavi, Haifa (IL); Elad Ratzabi, Ramat Gan (IL); Aviv Ellman, Kfar-Saba (IL); Timothy M. Conkin, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 254 days.

(21) Appl. No.: 16/244,330

(22) Filed: Jan. 10, 2019

(65) Prior Publication Data
US 2020/0222127 A1    Jul. 16, 2020

(51) Int. Cl.
*A61B 34/30*    (2016.01)
*A61B 34/20*    (2016.01)
*A61B 90/00*    (2016.01)

(52) U.S. Cl.
CPC .............. *A61B 34/30* (2016.02); *A61B 90/37* (2016.02); *A61B 2034/2072* (2016.02); *A61B 2090/3983* (2016.02)

(58) Field of Classification Search
CPC .............. A61B 34/20; A61B 2090/363; A61B 2090/3983; A61B 5/064; A61B 5/1127;
(Continued)

(56) References Cited

U.S. PATENT DOCUMENTS

| 5,592,939 A | 1/1997 | Martinelli |
| 5,868,675 A | 2/1999 | Henrion et al. |
(Continued)

FOREIGN PATENT DOCUMENTS

| EP | 2783814 A2 | 10/2014 |
| EP | 2921267 A2 | 9/2015 |
| EP | 3613544 A1 | 2/2020 |

OTHER PUBLICATIONS

International Search Report and Written Opinion dated Apr. 9, 2020 in corresponding/related International Application No. PCT/US2020/012962.
(Continued)

*Primary Examiner* — Kenny A Cese
(74) *Attorney, Agent, or Firm* — Harness, Dickey & Pierce, P.L.C.

(57) ABSTRACT

Disclosed is a system for assisting in guiding and performing a procedure on a subject. The subject may be any appropriate subject such as inanimate object and/or an animate object. The guide and system may include various manipulable or movable members, such as robotic systems, and may be registered to selected coordinate systems.

7 Claims, 7 Drawing Sheets

(58) Field of Classification Search
CPC . A61B 34/30; A61B 90/37; A61B 2034/2072; G06T 2207/30204; G06T 7/80; G06T 7/74
See application file for complete search history.

(56) References Cited

U.S. PATENT DOCUMENTS

| | | |
|---|---|---|
| 5,913,820 A | 6/1999 | Bladen et al. |
| 5,983,126 A | 11/1999 | Wittkampf |
| 6,026,315 A | 2/2000 | Lenz et al. |
| 6,474,341 B1 | 11/2002 | Hunter et al. |
| 6,940,941 B2 | 9/2005 | Gregerson et al. |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 8,150,494 B2 | 4/2012 | Simon et al. |
| 8,175,681 B2 | 5/2012 | Hartmann et al. |
| 8,503,745 B2 | 8/2013 | Simon et al. |
| 8,737,708 B2 | 5/2014 | Hartmann et al. |
| 9,737,235 B2 | 8/2017 | Hartmann |
| 2004/0199072 A1 | 10/2004 | Sprouse et al. |
| 2009/0076655 A1 | 3/2009 | Blondel et al. |
| 2013/0274921 A1 | 10/2013 | Aiso |
| 2017/0265774 A1 | 9/2017 | Johnson et al. |
| 2018/0325610 A1* | 11/2018 | Cameron ............. A61B 5/1079 |
| 2019/0061163 A1* | 2/2019 | Yamaguchi ............ B25J 9/1664 |

OTHER PUBLICATIONS

U.S. Appl. No. 16/244,369, filed Jan. 10, 2019, Snyder et al.
International Search Report and Written Opinion dated May 4, 2020 in corresponding/related International Application No. PCT/US2020/012958.

* cited by examiner

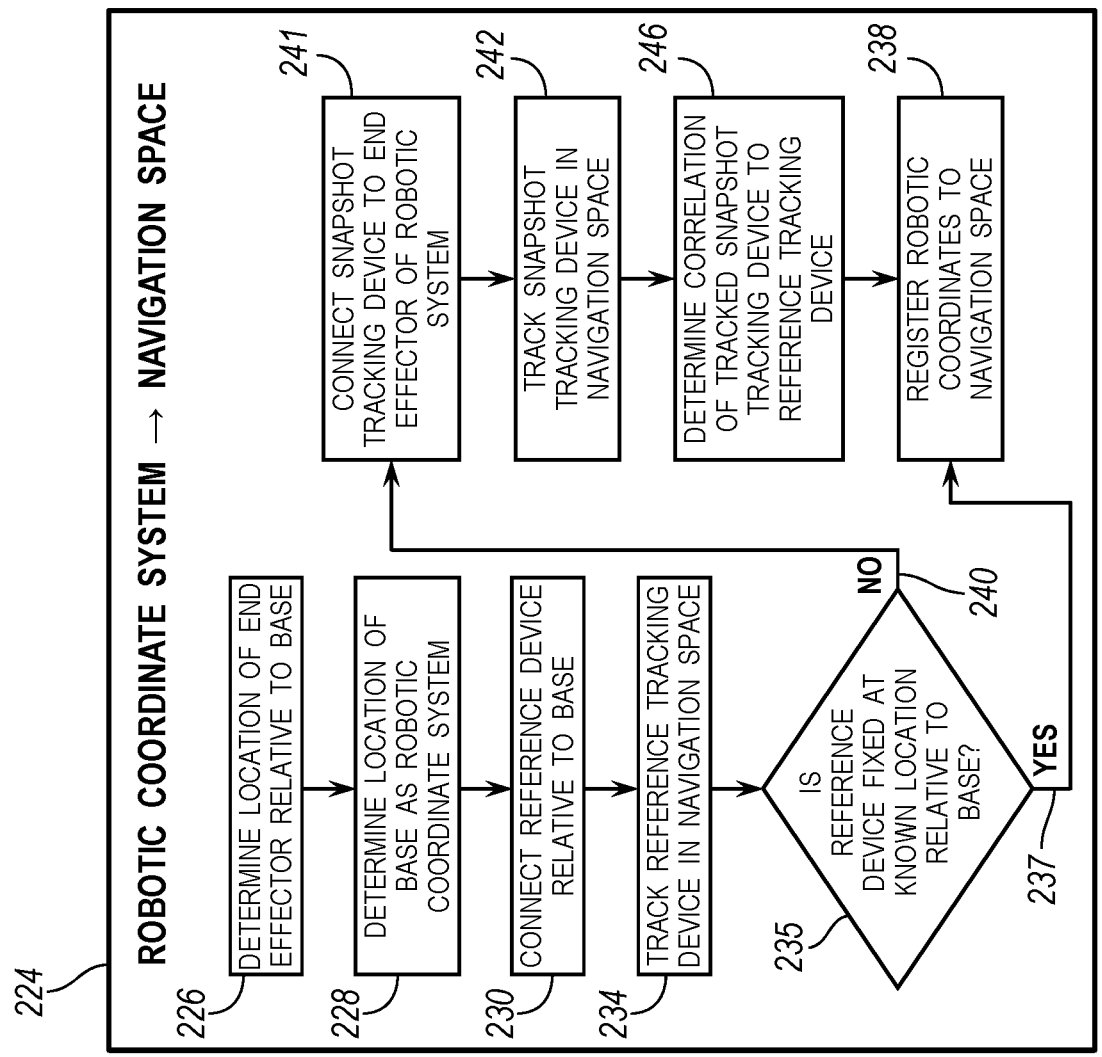
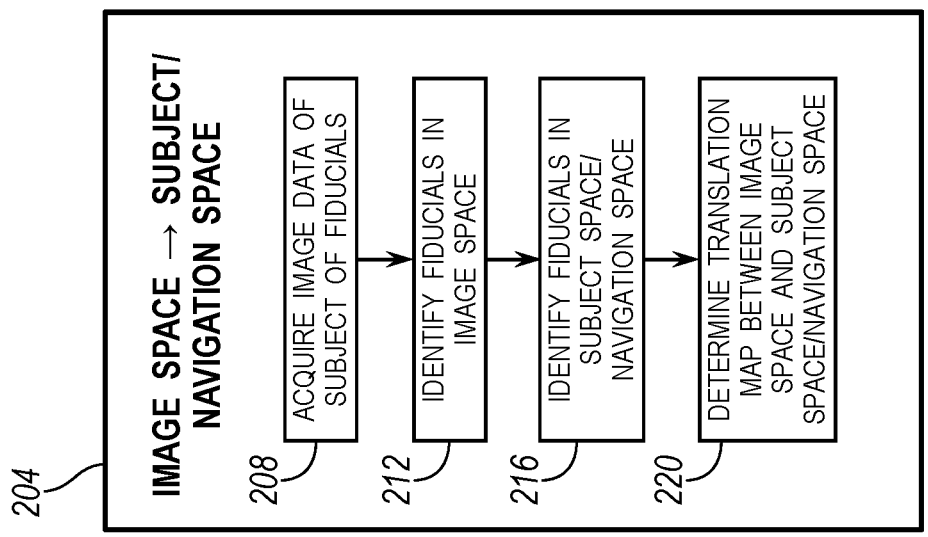
FIG. 6
FIG. 5

SYSTEM AND METHOD FOR REGISTRATION BETWEEN COORDINATE SYSTEMS AND NAVIGATION

CROSS-REFERENCE TO RELATED APPLICATIONS

This application includes subject matter similar to that disclosed in concurrently filed U.S. patent application Ser. No. 16/244,369. The entire disclosure of the above application is incorporated herein by reference.

FIELD

The subject disclosure is related generally to a tracking and navigation system, and particularly to registering coordinate systems.

BACKGROUND

This section provides background information related to the present disclosure which is not necessarily prior art.

An instrument can be navigated relative to a subject for performing various procedures. For example, the subject can include a patient on which a surgical procedure is being performed. During a surgical procedure, an instrument can be tracked in an object or subject space. In various embodiments the subject space can be a patient space defined by a patient. The location of the instrument that is tracked can be displayed on a display device relative to an image of the patient.

The position of the patient can be determined with a tracking system. Generally, a patient is registered to the image, via tracking an instrument relative to the patient to generate a translation map between the subject or object space (e.g. patient space) and the image space. This often requires time during a surgical procedure for a user, such as a surgeon, to identify one or more points in the subject space and correlating, often identical points, in the image space.

After registration, the position of the instrument can be appropriately displayed on the display device while tracking the instrument. The position of the instrument relative to the subject can be displayed as a graphical representation, sometimes referred to as an icon on the display device.

SUMMARY

This section provides a general summary of the disclosure, and is not a comprehensive disclosure of its full scope or all of its features.

According to various embodiments, a fiducial object can be imaged with an imaging system. The fiducial object may be connected to a selected system, such as a robotic system. The robotic system may include an appropriate robotic system, such as a Mazor X™ Robotic Guidance System, sold by Mazor Robotics Ltd. having a place of business in Israel and/or Medtronic, Inc. having a place of business in Minnesota, USA. The fiducial object may include one or more objects, such as an array of discrete objects. The discrete objects may include spheres, objects of various shapes, a continuous and/or one or more rods that can all be in one or intersect one plane. The fiducial object can be modeled in three-dimensional (3D) space as a 3D model. Fiducial features can be extracted from the 3D model. The fiducial features can be compared to or coordinated with image fiducial features that are the imaged fiducial object or some portion thereof (e.g. an image fiducial feature can be a point relating to a center of a sphere or a circle or point relating to an intersection of a rod with a plane).

In various embodiments, the different systems used relative to the subject may include different coordinate systems (e.g. locating systems). For example, a robotic system may be moved relative to a subject that includes a robotic coordinate system. The robot may be fixed, including removably fixed, at a position relative to the subject. Thus, movement of a portion of the robot relative to the base of the robot (i.e. the fixed portion of the robot) may be known due to various features of the robot. For example, encoders (e.g. optical encoders, potentiometer encoders, or the like) may be used to determine movement or amount of movement of various joints (e.g. pivots) of a robot. A position of an end effector (e.g. a terminal end) of the robot may be known relative to the base of the robot. Given a known position of the subject relative to the base and the immovable relative position of the base and the subject, the position of the end effector relative to the subject may be known during movement of a robot and/or during a stationary period of the end effector. Thus, the robot may define a coordinate system relative to the subject.

Various other portions may also be tracked relative to the subject. For example, a tracking system may be incorporated into a navigation system that includes one or more instruments that may be tracked relative to the subject. The navigation system may include one or more tracking systems that track various portions, such as tracking devices, associated with instruments. The tracking system may include a localizer that is configured to determine the position of the tracking device in a navigation system coordinate system. Determination of the navigation system coordinate system may include those described at various references including U.S. Pat. Nos. 8,737,708; 9,737,235; 8,503,745; and 8,175,681; all incorporated herein by reference. In particular, a localizer may be able to track an object within a volume relative to the subject. The navigation volume, in which a device, may be tracked may include or be referred to as the navigation coordinate system or navigation space. A determination or correlation between the two coordinate systems may allow for or also be referred to as a registration between two coordinate systems.

In various embodiments the first coordinate system, which may be a robotic coordinate system, may be registered to a second coordinate system, which may be a navigation coordinate system. Accordingly, coordinates in one coordinate system may then be transformed to a different or second coordinate system due to a registration. Registration may allow for the use of two coordinate systems and/or the switching between two coordinate systems. For example, during a procedure a first coordinate system may be used for a first portion or a selected portion of a procedure and a second coordinate system may be used during a second portion of a procedure. Further, two coordinate systems may be used to perform or track a single portion of a procedure, such as for verification and/or collection of additional information.

Furthermore, images may be acquired of selected portions of a subject. The images may be displayed for viewing by a user, such as a surgeon. The images may have superimposed on a portion of the image a graphical representation of a tracked portion or member, such as an instrument. According to various embodiments, the graphical representation may be superimposed on the image at an appropriate position due to registration of an image space (also referred to as an image coordinate system) to a subject space. A method to register a subject space defined by a subject to an image space may include those disclosed in U.S. Pat. Nos. 8,737,708; 9,737,235; 8,503,745; and 8,175,681; all incorporated herein by reference.

During a selected procedure, the first coordinate system may be registered to the subject space or subject coordinate system due to a selected procedure, such as imaging of the subject. In various embodiments the first coordinate system may be registered to the subject by imaging the subject with a fiducial portion that is fixed relative to the first member or system, such as the robotic system. The known position of the fiducial relative to the robotic system may be used to register the subject space relative to the robotic system due to the image of the subject including the fiducial portion. Thus, the position of the robotic system or a portion thereof, such as the end effector, may be known or determined relative to the subject. Due to registration of a second coordinate system to the robotic coordinate system may allow for tracking of additional elements not fixed to the robot relative to a position determined or tracked by the robot.

The tracking of an instrument during a procedure, such as a surgical or operative procedure, allows for navigation of a procedure. When image data is used to define an image space it can be correlated or registered to a physical space defined by a subject, such as a patient. According to various embodiments, therefore, the patient defines a patient space in which an instrument can be tracked and navigated. The image space defined by the image data can be registered to the patient space defined by the patient. The registration can occur with the use of fiducials that can be identified in the image data and in the patient space.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is a flow chart of an image space to patient space registration;

FIG. 6 is a flow chart of a robotic coordinate system to a navigation coordinate system registration;

Corresponding reference numerals indicate corresponding parts throughout the several views of the drawings.

DETAILED DESCRIPTION

Example embodiments will now be described more fully with reference to the accompanying drawings.

The subject disclosure is directed to an exemplary embodiment of a surgical procedure on a subject, such as a human patient. It is understood, however, that the system and methods described herein are merely exemplary and not intended to limit the scope of the claims included herein. In various embodiments, it is understood, that the systems and methods may be incorporated into and/or used on non-animate objects. The systems may be used to, for example, to register coordinate systems between two systems for use on manufacturing systems, maintenance systems, and the like. For example, automotive assembly may use one or more robotic systems including individual coordinate systems that may be registered together for coordinated or consorted actions. Accordingly, the exemplary illustration of a surgical procedure herein is not intended to limit the scope of the appended claims.

Discussed herein, according various embodiments, are processes and systems for allowing registration between various coordinate systems. In various embodiments, a robotic or first coordinate system may be registered to an image coordinate system or space. A navigation space or coordinate system may then be registered to the robotic or first coordinate system and, therefore, be registered to the image coordinate system without being separately or independently registered to the image space. Similarly, the navigation space or coordinate system may be registered to the image coordinate system or space directly or independently. The robotic or first coordinate system may then be registered to the navigation space and, therefore, be registered to the image coordinate system or space without being separately or independently registered to the image space.

Figure 1:
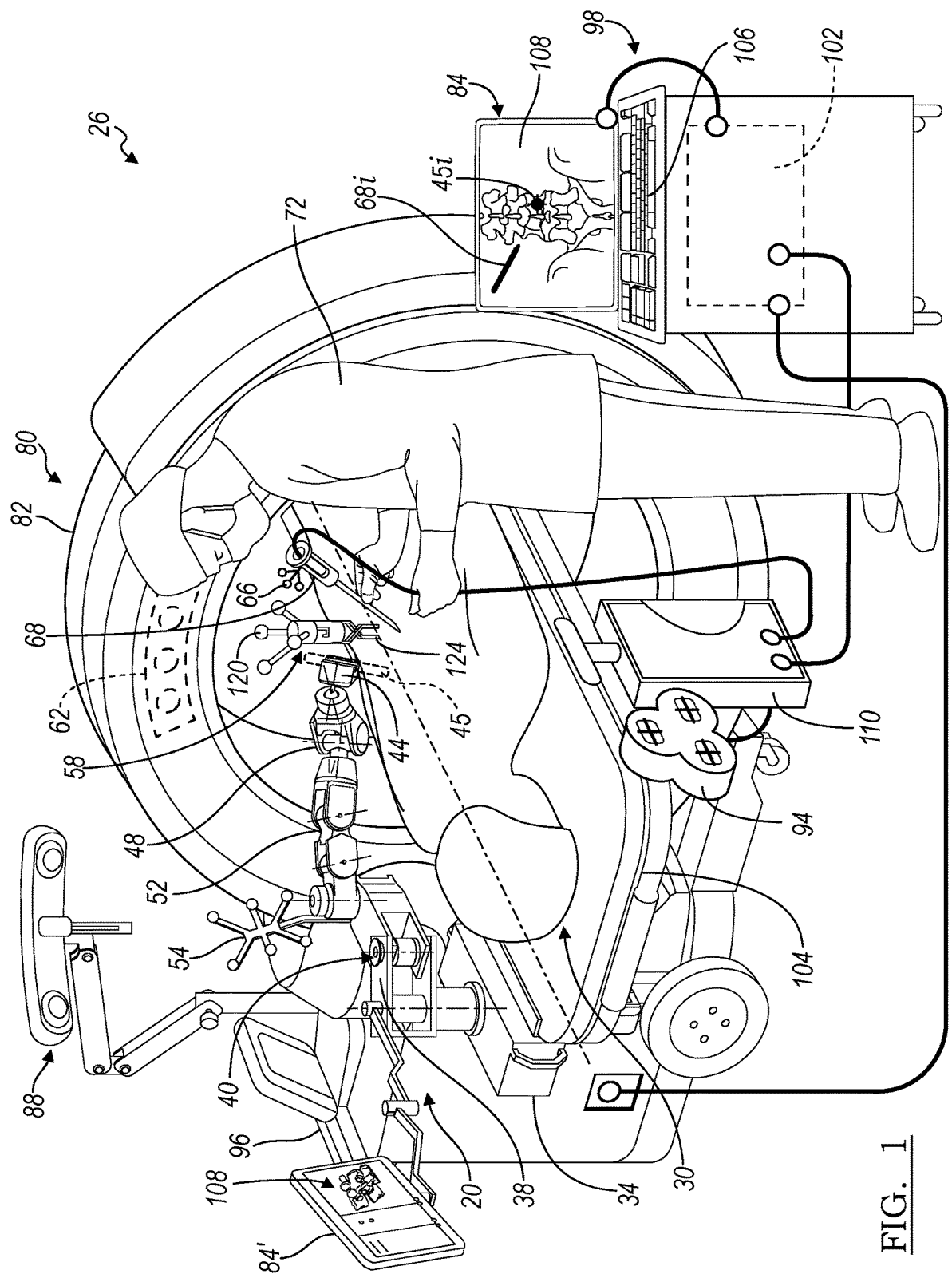
FIG. 1 is diagrammatic view illustrating an overview of a robotic system and a navigation system, according to various embodiments.

FIG. 1 is a diagrammatic view illustrating an overview of a procedure room or arena. In various embodiments, the procedure room may include a surgical suite in which may be placed a robotic system 20 and a navigation system 26 that can be used for various procedures. The robotic system 20 may include a Mazor X™ robotic guidance system, sold by Medtronic, Inc. The robotic system 20 may be used to assist in guiding selected instrument, such as drills, screws, etc. relative to a subject 30. The robotic system 20 may include a mount 34 that fixes a portion, such as a robotic base 38, relative to the subject 30. The robotic system 20 may include one or more arms 40 that are moveable or pivotable relative to the subject 30, such as including an end effector 44. The end effector may be any appropriate portion, such as a tube, guide, or passage member. The end effector 44 may be moved relative to the base 38 with one or more motors. The position of the end effector 44 may be known or determined relative to the base 38 with one or more encoders at one or more joints, such as a wrist joint 48 and/or an elbow joint 52 of the robotic system 20.

The navigation system 26 can be used to track the location of one or more tracking devices, tracking devices may include a robot tracking device 54, a subject tracking device 58, an imaging system tracking device 62, and/or an tool tracking device 66. A tool 68 may be any appropriate tool such as a drill, forceps, or other tool operated by a user 72. The tool 68 may also include an implant, such as a spinal implant or orthopedic implant. It should further be noted that the navigation system 26 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 26 and the various instruments may be used in any appropriate procedure, such as one that is generally minimally invasive or an open procedure.

An imaging device 80 may be used to acquire pre-, intra-, or post-operative or real-time image data of a subject, such as the subject 30. It will be understood, however, that any appropriate subject can be imaged and any appropriate procedure may be performed relative to the subject. In the example shown, the imaging device 80 comprises an O-Arm® imaging device sold by Medtronic Navigation, Inc. having a place of business in Louisville, Colo., USA. The imaging device 80 may have a generally annular gantry housing 82 in which an image capturing portion is moveably placed. The image capturing portion may include an x-ray source or emission portion and an x-ray receiving or image receiving portion located generally or as practically possible 180 degrees from each other and mounted on a rotor relative to a track or rail. The image capturing portion can be operable to rotate 360 degrees during image acquisition. The image capturing portion may rotate around a central point or axis, allowing image data of the subject 80 to be acquired from multiple directions or in multiple planes. The imaging device 80 can include those disclosed in U.S. Pat. Nos. 7,188,998; 7,108,421; 7,106,825; 7,001,045; and 6,940,941; all of which are incorporated herein by reference, or any appropriate portions thereof. In one example, the imaging device 80 can utilize flat plate technology having a 1,720 by 1,024 pixel viewing area.

The position of the imaging device 80, and/or portions therein such as the image capturing portion, can be precisely known relative to any other portion of the imaging device 80. The imaging device 80, according to various embodiments, can know and recall precise coordinates relative to a fixed or selected coordinate system. This can allow the imaging system 80 to know its position relative to the patient 30 or other references. In addition, as discussed herein, the precise knowledge of the position of the image capturing portion can be used in conjunction with a tracking system to determine the position of the image capturing portion and the image data relative to the tracked subject, such as the patient 30.

The imaging device 80 can also be tracked with a tracking device 62. The image data defining an image space acquired of the patient 30 can, according to various embodiments, be inherently or automatically registered relative to an object space. The object space can be the space defined by a patient 30 in the navigation system 26. The automatic registration can be achieved by including the tracking device 62 on the imaging device 80 and/or the determinable precise location of the image capturing portion. According to various embodiments, as discussed herein, imagable portions, virtual fiducial points and other features can also be used to allow for registration, automatic or otherwise. It will be understood, however, that image data can be acquired of any subject which will define subject space. Patient space is an exemplary subject space. Registration allows for a translation between patient space and image space.

The patient 80 can also be tracked as the patient moves with a patient tracking device, DRF, or tracker 58. Alternatively, or in addition thereto, the patient 30 may be fixed within navigation space defined by the navigation system 26 to allow for registration. As discussed further herein, registration of the image space to the patient space or subject space allows for navigation of the instrument 68 with the image data. When navigating the instrument 68, a position of the instrument 68 can be illustrated relative to image data acquired of the patient 30 on a display device 84. Various tracking systems, such as one including an optical localizer 88 or an electromagnetic (EM) localizer 92 can be used to track the instrument 68.

More than one tracking system can be used to track the instrument 68 in the navigation system 26. According to various embodiments, these can include an electromagnetic tracking (EM) system having the EM localizer 94 and/or an optical tracking system having the optical localizer 88. Either or both of the tracking systems can be used to tracked selected tracking devices, as discussed herein. It will be understood, unless discussed otherwise, that a tracking device can be a portion trackable with a selected tracking system. A tracking device need not refer to the entire member or structure to which the tracking device is affixed or associated.

It is further appreciated that the imaging device 80 may be an imaging device other than the O-Arm® imaging device and may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

In various embodiments, an imaging device controller 96 may control the imaging device 80 and can receive the image data generated at the image capturing portion and store the images for later use. The controller 96 can also control the rotation of the image capturing portion of the imaging device 80. It will be understood that the controller 96 need not be integral with the gantry housing 82, but may be separate therefrom. For example, the controller may be a portions of the navigation system 26 that may include a processing and/or control system 98 including a processing unit or processing portion 102. The controller 96, however, may be integral with the gantry 82 and may include a second and separate processor, such as that in a portable computer.

The patient 30 can be fixed onto an operating table 104. According to one example, the table 104 can be an Axis Jackson® operating table sold by OSI, a subsidiary of Mizuho Ikakogyo Co., Ltd., having a place of business in Tokyo, Japan or Mizuho Orthopedic Systems, Inc. having a place of business in California, USA. Patient positioning devices can be used with the table, and include a Mayfield® clamp or those set forth in commonly assigned U.S. patent application Ser. No. 10/405,068 entitled "An Integrated Electromagnetic Navigation And Patient Positioning Device", filed Apr. 1, 2003 which is hereby incorporated by reference.

The position of the patient 30 relative to the imaging device 80 can be determined by the navigation system 26. The tracking device 62 can be used to track and locate at least a portion of the imaging device 80, for example the gantry or housing 82. The patient 30 can be tracked with the dynamic reference frame 58, as discussed further herein. Accordingly, the position of the patient 30 relative to the imaging device 80 can be determined. Further, the location of the imaging portion can be determined relative to the housing 82 due to its precise position on the rail within the housing 82, substantially inflexible rotor, etc. The imaging device 80 can include an accuracy of within 10 microns, for example, if the imaging device 80 is an O-Arm® imaging device sold by Medtronic Navigation, Inc. having a place of business in Louisville, Colo. Precise positioning of the imaging portion is further described in U.S. Pat. Nos. 7,188,998; 7,108,421; 7,106,825; 7,001,045; and 6,940,941; all of which are incorporated herein by reference, According to various embodiments, the imaging device 80 can generate and/or emit x-rays from the x-ray source that propagate through the patient 30 and are received by the x-ray imaging receiving portion. The image capturing portion generates image data representing the intensities of the received x-rays. Typically, the image capturing portion can include an image intensifier that first converts the x-rays to visible light and a camera (e.g. a charge couple device) that converts the visible light into digital image data. The image capturing portion may also be a digital device that converts x-rays directly to digital image data for forming images, thus potentially avoiding distortion introduced by first converting to visible light.

Two dimensional and/or three dimensional fluoroscopic image data that may be taken by the imaging device 80 can be captured and stored in the imaging device controller 96. Multiple image data taken by the imaging device 80 may also be captured and assembled to provide a larger view or image of a whole region of a patient 30, as opposed to being directed to only a portion of a region of the patient 30. For example, multiple image data of the patient's 30 spine may be appended together to provide a full view or complete set of image data of the spine.

The image data can then be forwarded from the image device controller 96 to the navigation computer and/or processor system 102 that can be a part of a controller or work station 98 having the display 84 and a user interface 106. It will also be understood that the image data is not necessarily first retained in the controller 96, but may also be directly transmitted to the work station 98. The work station 98 can provide facilities for displaying the image data as an image 108 on the display 84, saving, digitally manipulating, or printing a hard copy image of the received image data. The user interface 106, which may be a keyboard, mouse, touch pen, touch screen or other suitable device, allows the user 72 to provide inputs to control the imaging device 80, via the image device controller 96, or adjust the display settings of the display 84. The work station 98 may also direct the image device controller 96 to adjust the image capturing portion of the imaging device 80 to obtain various two-dimensional images along different planes in order to generate representative two-dimensional and three-dimensional image data.

With continuing reference to FIG. 1, the navigation system 26 can further include the tracking system including either or both of the electromagnetic (EM) localizer 94 and/or the optical localizer 88. The tracking systems may include a controller and interface portion 110. The controller 110 can be connected to the processor portion 102, which can include a processor included within a computer. The EM tracking system may include the STEALTHSTATION® AXIEM™ Navigation System, sold by Medtronic Navigation, Inc. having a place of business in Louisville, Colo.; or can be the EM tracking system described in U.S. patent application Ser. No. 10/941,782, filed Sep. 15, 2004, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 26 may also be or include any appropriate tracking system, including a STEALTHSTATION® TREON® or S7™ tracking systems having an optical localizer, that may be used as the optical localizer 88, and sold by Medtronic Navigation, Inc. of Louisville, Colo. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 80, etc. Alternatively, various portions, such as the instrument 68 may employ a wireless communications channel, such as that disclosed in U.S. Pat. No. 6,474,341, entitled "Surgical Communication Power System," issued Nov. 5, 2002, herein incorporated by reference, as opposed to being coupled directly to the controller 110. Also, the tracking devices 62, 66, 54 can generate a field and/or signal that is sensed by the localizer(s) 88, 94.

Various portions of the navigation system 26, such as the instrument 68, and others as will be described in detail below, can be equipped with at least one, and generally multiple, of the tracking devices 66. The instrument can also include more than one type or modality of tracking device 66, such as an EM tracking device and/or an optical tracking device. The instrument 68 can include a graspable or manipulable portion at a proximal end and the tracking devices may be fixed near the manipulable portion of the instrument 68.

Additional representative or alternative localization and tracking system is set forth in U.S. Pat. No. 5,983,126, entitled "Catheter Location System and Method," issued Nov. 9, 1999, which is hereby incorporated by reference. The navigation system 26 may be a hybrid system that includes components from various tracking systems.

According to various embodiments, the navigation system 26 can be used to track the instrument 68 relative to the patient 30. The instrument 68 can be tracked with the tracking system, as discussed above. Image data of the patient 30, or an appropriate subject, can be used to assist the user 72 in guiding the instrument 68. The image data, however, is registered to the patient 30. The image data defines an image space that is registered to the patient space defined by the patient 30. The registration can be performed as discussed herein, automatically, manually, or combinations thereof.

Generally, registration allows a translation map to be generated of the physical location of the instrument 68 relative to the image space of the image data. The translation map allows the tracked position of the instrument 68 to be displayed on the display device 84 relative to the image data 108. A graphical representation 68*i*, also referred to as an icon, can be used to illustrate the location of the instrument 68 relative to the image data 108.

Figure 2:
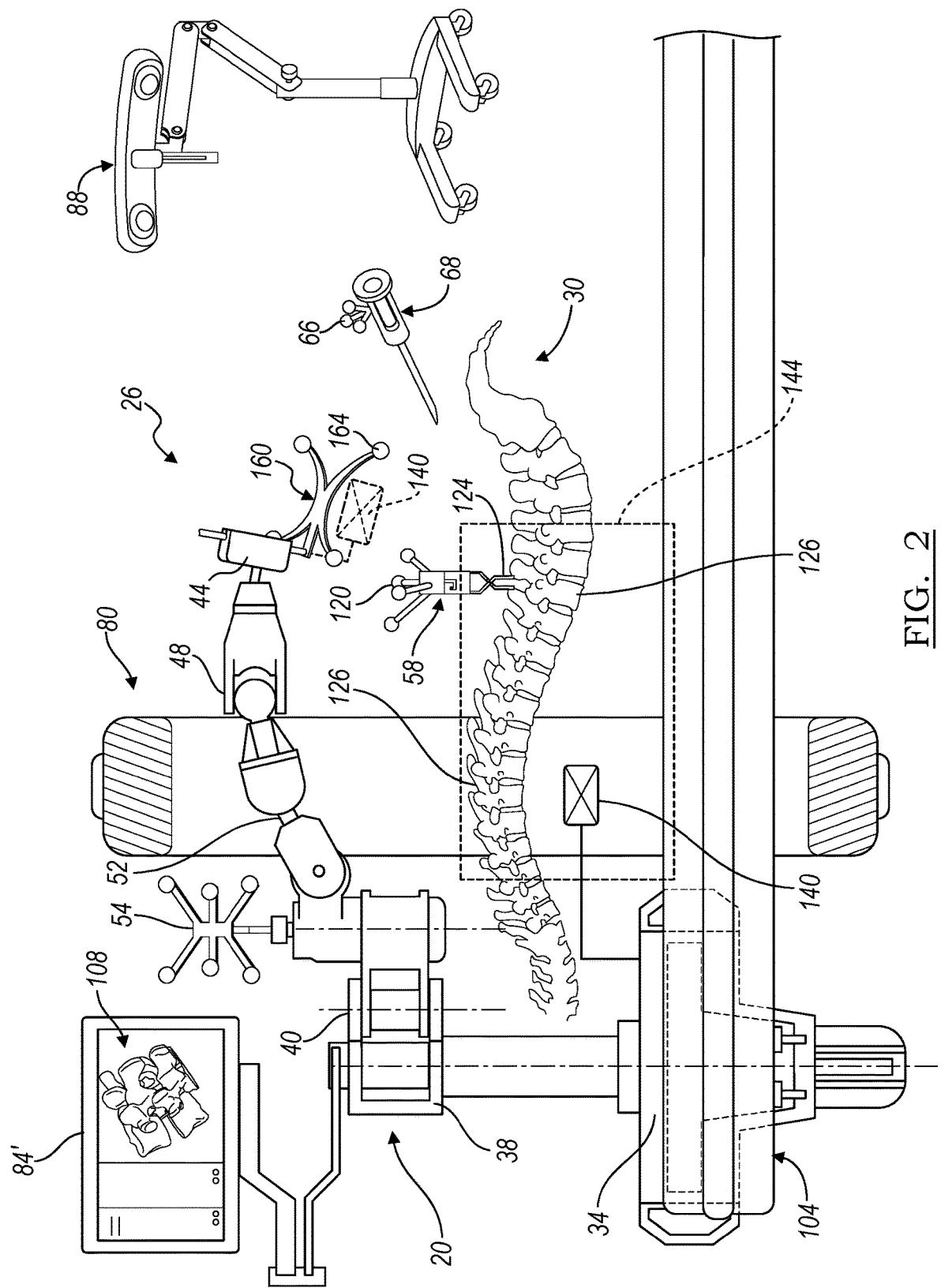
FIG. 2 is a detailed environmental view of a robotic system and a tracking system, according to various embodiments.
Figure 3:
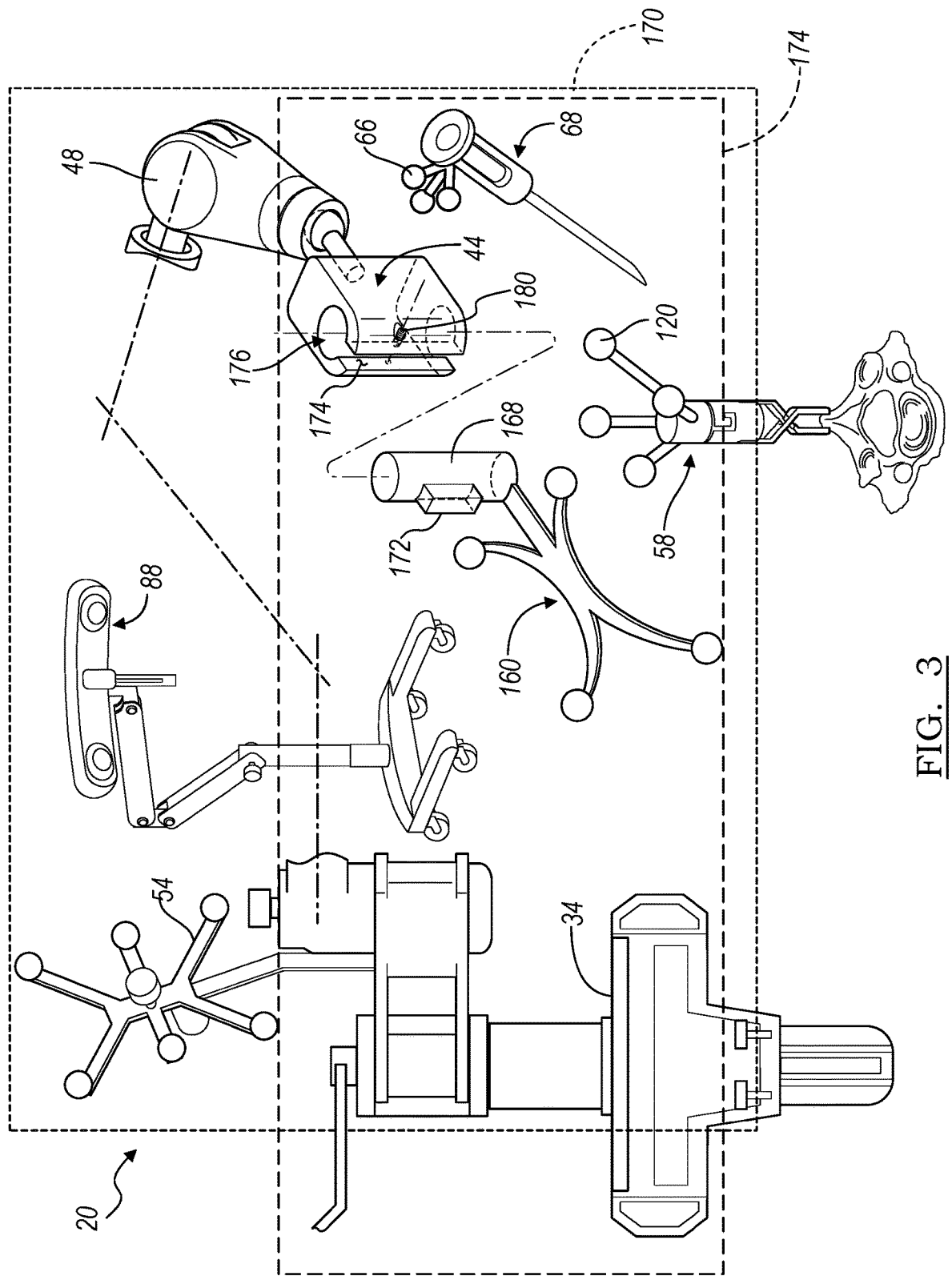
FIG. 3 is a detailed view of a robotic system with a snapshot tracking device, according to various embodiments.
Figure 4:
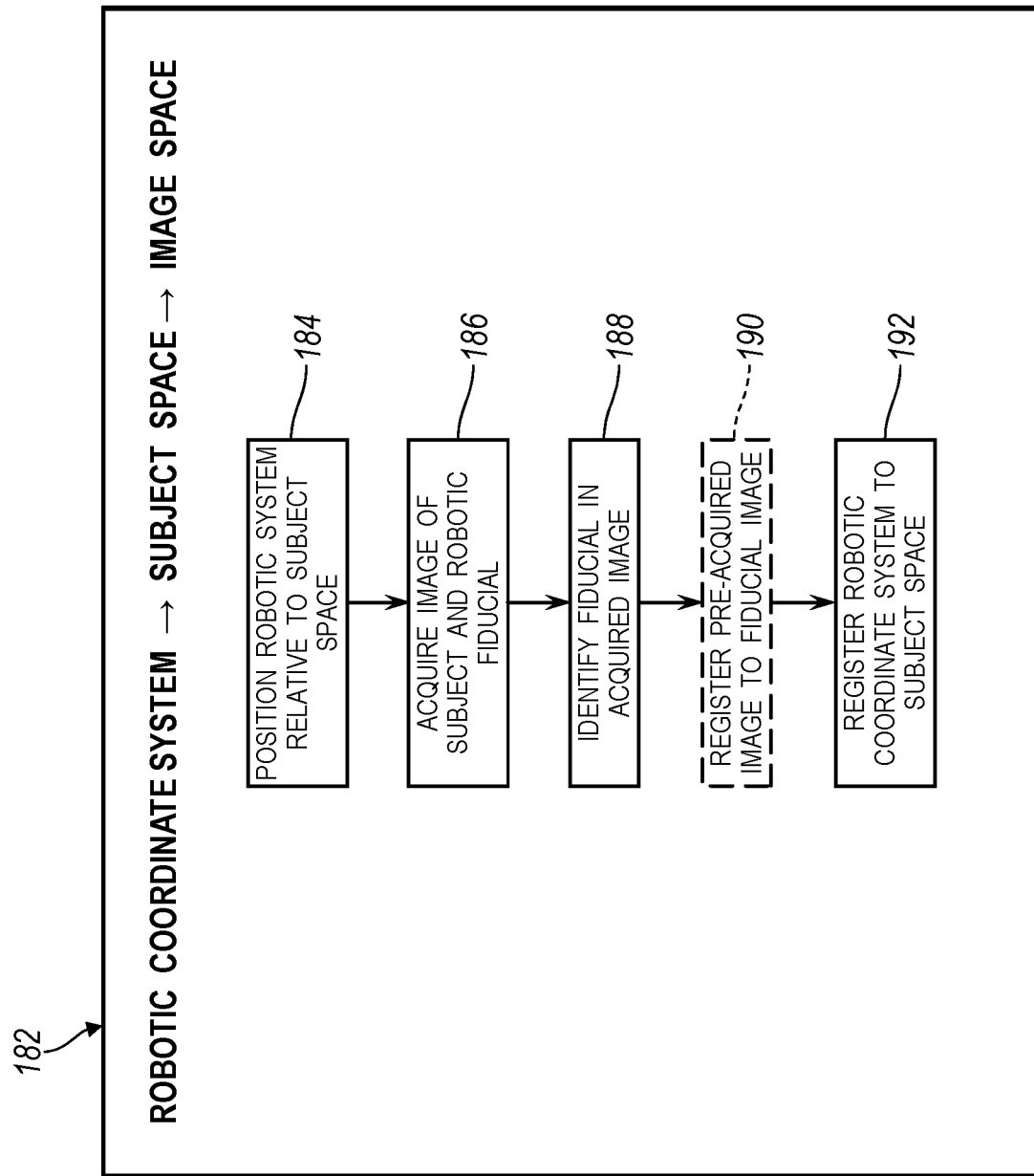
FIG. 4 is a flow chart of a method of registering a robotic space to an image space.

With continuing reference to FIG. 1 and additional reference to FIG. 2 and FIG. 3, a subject registration system or method can use the tracking device 58. The tracking device 58 may include portions or members 120 that may be trackable, but may also act as or be operable as a fiducial assembly. The fiducial assembly 120 can include a clamp or other fixation portion 124 and the imagable fiducial body 120. It is understood, however, that the members 120 may be separate from the tracking device 58. The fixation portion 124 can be provided to fix any appropriate portion, such as a portion of the anatomy. As illustrated in FIGS. 1 and 2, the fiducial assembly 120 can be interconnected with a portion of a spine 126 such as a spinous process 130.

The fixation portion 124 can be interconnected with a spinous process 130 in any appropriate manner. For example, a pin or a screw can be driven into the spinous process 130. Alternatively, or in addition thereto, a clamp portion 124 can be provided to interconnect the spinous process 130. The fiducial portions 120 may be imaged with the imaging device 80. It is understood, however, that various portions of the subject (such as a spinous process) may also be used as a fiducial portion.

In various embodiments, when the fiducial portions 120 are imaged with the imaging device 80, image data is generated that includes or identifies the fiducial portions 120. The fiducial portions 120 can be identified in image data automatically (e.g. with a processor executing a program), manually (e.g. by selection an identification by the user 72), or combinations thereof (e.g. by selection an identification by the user 72 of a seed point and segmentation by a processor executing a program). Methods of automatic imagable portion identification include those disclosed in U.S. Pat. No. 8,150,494 issued on Apr. 3, 2012, incorporated herein by reference. Manual identification can include selecting an element (e.g. pixel) or region in the image data wherein the imagable portion has been imaged. Regardless, the fiducial portions 120 identified in the image data can be used as fiducial points or positions that can be used to register the image data or the image space of the image data with patient space.

In various embodiments, to register an image space or coordinate system to another space or coordinate system, such as a navigation space, the fiducial portions 120 that are identified in the image 108 may then be identified in the subject space defined by the subject 30, in an appropriate manner. For example, the user 72 may move the instrument 68 relative to the subject 30 to touch the fiducial portions 120, if the fiducial portions are attached to the subject 30 in the same position during the acquisition of the image data to generate the image 108. It is understood that the fiducial portions 120, as discussed above in various embodiments, may be attached to the subject 30 and/or may include anatomical portions of the subject 30. Additionally, a tracking device may be incorporated into the fiducial portions 120 and they may be maintained with the subject 30 after the image is acquired. In this case, the registration or the identification of the fiducial portions 120 in a subject space may be made. Nevertheless, according to various embodiments, the user 72 may move the instrument 68 to touch the fiducial portions 120. The tracking system, such as with the optical localizer 88, may track the position of the instrument 68 due to the tracking device 66 attached thereto. This allows the user 72 to identify in the navigation space the locations of the fiducial portions 120 that are identified in the image 108. After identifying the positions of the fiducial portions 120 in the navigation space, which may include a subject space, the translation map may be made between the subject space defined by the subject 30 in a navigation space and the image space defined by the image 108. Accordingly, identical or known locations allow for registration as discussed further herein.

During registration, a translation map is determined between the image data coordinate system of the image data such as the image 108 and the patient space defined by the patient 30. Once the registration occurs, the instrument 68 can be tracked with the tracking system that is registered to the image data to allow an identification and illustration of a position of the tracked instrument 68 as an icon superimposed on the image data. Registration of the image 108 (or any selected image data) to the subject 30 may occur at any appropriate time.

After the registration of the image space to the patient space, the instrument 68 can be tracked relative to the image 108. As illustrated in FIG. 1, the icon 68i representing a position (which may include a 6 degree of freedom position (including 3D location and orientation)) of the instrument 68 can be displayed relative to the image 108 on the display 84. Due to the registration of the image space to the patient space, the position of the icon 68i relative to the image 108 can substantially identify or mimic the location of the instrument 68 relative to the patient 30 in the patient space. As discussed above, this can allow a navigated procedure to occur.

The robotic system 20 having the robotic system coordinate system may be registered to the navigation space coordinate system, as discussed herein, due to the reference tracking device 54 (e.g. if fixed to a known position on or relative to the robotic system 20) and/or due to the tracking of the snapshot tracking device 160. The snapshot tracking device 160 may include one or more trackable portions 164 that may be tracked with the localizer 88 or any appropriate localizer (e.g. optical, EM, radar). It is understood, however, that any appropriate tracking system may be used to track the snapshot tracking device 160. A fixed reference tracking device may also be positioned within the navigation space. The fixed navigation tracker may include the patient tracker 58 which may be connected to the patient 30 and/or the robot tracker 54 that may be fixed to the base 34 of the robotic system 20. The reference tracker, therefore, may be any appropriate tracker that is positioned relative to the snapshot tracker 160 that is within the navigation coordinate space during the registration period. For the discussion herein the robot tracker 54 will be referred to however, the patient tracker 58 may also be used as the reference tracker. Further, reference tracker may be positioned within the coordinate system at any position relative to the snapshot tracker 160 as long as the snapshot tracker 160 may be tracked relative to the reference tracker.

In various embodiments, the snapshot tracker 160 may be positioned at a known position relative to the end effector 44. For example, the snapshot tracker 160, as illustrated in FIG. 3, which includes the trackable portions 164, extends from a rod or connection member 168. The connection member 168 may include a keyed portion, such as a projection 172 that may engage a slot 174 of the end effector 44. The end effector 44 may form or define a cannula or passage 176 that may engage the connector 168. The connector 168 may be positioned within the passage 176 of the end effector 44. The connector 168 may then be fixed to the end effector 44, such as with a fixation member including a set screw or clamping of the end effector 44, such as with a set screw or clamping member 180. The projection 172 may engage within the slot 174 to fix the snapshot tracker 160 rotationally relative to the end effector 44. The connector 168 positioned within the passage 176 and locked in place with the set screw 180 may then rigidly fix the snapshot tracking device 160 relative to the end effector 44. Thus, the position of the snapshot tracker 160 relative to the end effector 44 may be fixed.

The localizer 88 may then view or determine a position of the snapshot tracking device 160 relative to the reference tracking device 54 and or the reference tracking device 58. As the localizer 88 defines or may be used to define the navigation space, determining or tracking a position of the snapshot localizer 160 relative to the reference frame 54 may be used to determine a relationship between a position within the navigation space and the robotic space of the end effector 44.

With continuing reference to FIG. 3, therefore, the navigation space defined by the localizer 88 may include the full navigation space 170 which may include portions relative to the subject, such as the subject tracker 58 and other portions that may be moved therein, such as the instrument 68. The robotic registration space may be smaller and may include a robotic registration space 174 that may include the reference frame 54 and the snapshot tracker 160. As discussed above, however, the robot registration navigation space may include the snapshot tracker 160 and the patient tracker 58 for registration. Accordingly, the exemplary registration navigation space 174 is merely for the current discussion. As discussed herein, both the robotic reference tracker 54 and the patient tracker 58 need not be used simultaneously. This is particularly true when the patient 30 is fixed in space, such as fixed relative to the robotic system 20.

With continuing reference to FIG. 2 and FIG. 3, and additional reference to FIGS. 4-8, a process or method of coordinating or registering a robotic coordinate system of the robotic system 20 to a navigation space or navigation coordinate system of the navigation system 26 is described. The registration may include various portions or sub-parts, as discussed herein. The various parts may occur in any appropriate order, and the order discussed herein is merely exemplary. The co-registration may further allow only one coordinate system of the robotic or navigation to be registered to a third coordinate system, such as an image coordinate system, but allow the registration of the other to the third coordinate system.

The robotic system 20, as discussed above, is positioned relative to the subject 30 for various portions of a procedure. In various embodiments, the robotic system 20 may be registered to the subject 30 and to the image 108 of the subject 30, that may be displayed on the display device 84 and/or a second or auxiliary display device 84' that may be movable relative to the robotic system 20. The imaging system 80, or any appropriate imaging system, may be used to image the subject 30. The image may include a portion of the subject, such as one or more of the vertebrae 126 and a fiducial or robotic fiducial array 140 that may be fixed to the robotic system 20. The robotic fiducial 140 may be fixed to a selected portion of the robotic system 20, such as to the base 34 and/or the fixed portion 38. The robotic fiducial 140 may also and/or alternatively be connected to the end effector 44 (illustrated in phantom in FIG. 2). The robotic fiducial 140 may be positioned relative to the subject 30 for acquisition of images such that the fiducial 140 is apparent in the images. Upon acquisition of the image of the robotic fiducial 140 and portions of the subject 30, such as the vertebrae 126, the position of the robotic fiducial 140 relative to the vertebrae 126 may be determined. If the robotic fiducial 140 is fixed to the robotic system 20, the robotic coordinate system may be determined relative to the subject space coordinate system. In various embodiments, if the fiducial 140 is connected to the end effector 44, the known position of the end effector in the robotic coordinate system allows for image registration to the robotic coordinate system of the robotic system 20. With continuing reference to FIG. 2 and additional reference to FIG. 4, the robotic coordinate system may be registered to a subject space or coordinate system in the method 182 as described.

Generally, the registration may include positioning the robotic system 20 relative to a subject space in block 184. Positioning of the robotic system 20 relative to the subject space may include positioning the robotic system 30 relative to the subject, as illustrated in FIG. 2. Further, positioning of the robotic system 20 may include positioning or removably positioning the robotic fiducial 140 relative to the subject 30. The robotic fiducial 140 may be removably placed in a position relative to the robotic system 20 for various procedures and may be substantially positioned in the same position for different or subsequent procedures. With the subject 30 positioned relative to the robotic system 20, fiducial images may be acquired of the subject 30 and the robotic fiducial 140 with the imaging system 80 in block 186. The acquisition of the fiducial images in block 186 allows for image data to be acquired of the subject 30, such as with the vertebrae 126, and the fiducial 140.

After acquisition of the robotic fiducial image in block 186, identifying of the robotic fiducial 140 in the acquired fiducial images occurs in block 188. Identification of the robotic fiducial in the robotic fiducial images may be manual, automatic, or a combination of automatic and manual. For example, the user may identify the robotic fiducial in the image a selected automatic system may segment the fiducials from the fiducial images, or the user may identify a seed pixel or voxel or multiple seed pixels or voxels and the processor system may further segment the fiducial system.

In various embodiments, the acquired images in block 186 may be used for planning and/or performing a procedure. For example, the imaging system 80 may acquire image data sufficient for a selected procedure. Thus, the images acquired in block 186 may be used for planning and navigating a selected procedure relative to the subject 30. The image data may include two-dimensional image data, reconstructed three-dimensional image data, and/or image data acquired over time to illustrate movement of motion of the subject (which may be acquired in 2D or 3D).

In various embodiments, however, the fiducial image acquired in block 186 may be optionally registered to other-time or pre-acquired images in block 190, such as an MRI or a computed tomography scan of the subject 30 prior to the acquisition of the fiducial images in block 186. The pre-acquired images may be acquired at any appropriate time prior to the acquisition of the fiducial images in block 186. It is understood, however, that the images may be acquired after the fiducial images and may be registered to the fiducial images in a similar manner as discussed herein. The registration of the fiducial images to the pre-acquired images may occur in any appropriate manner such as segmentation of selected vertebrae, identification in registration of selected fiducial elements in the images (e.g. anatomical fiducial portions and/or positioned or implanted fiducial members) or other appropriate procedures. Generally, the Mazor X® Robotic System may generally allow for registration of a pre-acquired image to the fiducial images and may be appropriate for registering the fiducial images in block 186 to the pre-acquired images in the registration of the pre-acquired image to the fiducial image in block 190.

The robotic coordinate system may also be registered to the subject space in block 192 with the identification of fiducials in the image in block 188 and the registration. The robotic fiducial 140, imaged with the fiducial images in block 186, is positioned in a known position relative to the robotic system 20, such as the base 34 and/or with the known position of the end effector 44 in the robotic coordinate system. The robotic coordinate system that is defined by the robotic system 20 relative to the base 34 and/or the fixed portion 38 may, therefore also, be pre-determined or known relative to the robotic fiducial 140 as the robotic fiducial 140 is fixed relative to the robotic system 20. When position with the end effector 44, the position of the robotic fiducial 140 is known in the robotic coordinate system by tracked (e.g. robotic system tracking) movement of the end effector 44. The fiducial image acquired in block 186 may also assist in defining the patient space relative to which the robotic system 20, particularly the end effector movable portion 44, may move is also then known. As discussed above, the end effector 44 moves in the robotic coordinate system due to the robotic tracking system that may include various mechanisms, such as encoders at the various movable portions, such as the wrist 48 or elbow 52, of the robotic system 20. If the fiducial images in block 186 are the images for performing the procedure, such as for navigation and may the displayed image 108, the registration may be substantially automatic as the subject 30 may be substantially fixed relative to the robotic system 20 (e.g. with a fixation ember extending from the base 38) and connected to the subject 30, such as the vertebrae 126.

Accordingly the robotic coordinate system can be registered to the subject space and/or image space according to the method 182. Given the registration of the robotic coordinate system to the image space the robotic, coordinate system registration may be used to determine a position of the end effector 44 and/or a member positioned through or with the end effector 44, relative to the image 108. Accordingly, the image 108 may be used to display a graphical representation, such as a graphical representation of the member or instrument 45 as an icon 45i superimposed or superimposed relative to the image 108.

With reference to FIG. 5, a flow chart for registration of an image space or image coordinate system and a navigation space defined by the localizer 88 is illustrated. The method 200 may include various sub-portions or sub-steps, including those as discussed above. It is understood that various sub-steps may occur in any appropriate order, and the order illustrated in FIG. 5 is merely exemplary. Generally a translation or registration between the image coordinate system and the navigation coordinate system may occur at any point that the two coordinate systems may be positioned or determined relative to one another.

The method 200 includes an image to patient registration. As discussed above, the image to patient registration may include acquiring image data of a subject, such as the subject 34, with fiducials in block 208. The image data of the subject 34 may be any appropriate image data, such as image data acquired with the imaging system 80. Further, the fiducials may include the fiducial portions 120, as discussed above, and/or appropriate anatomical portions of the subject 30. For example the fiducial portions may include portions of the anatomy such as the spinous process 130 of the subject 30. Nevertheless, the acquired image data may include the fiducials therein. Once the image data is acquired of the subject with the fiducials, identification of the fiducials in the image space may occur in block 212.

The identification of the fiducials in the image space may occur, as also discussed above. For example an automatic identification of the fiducials may be made in the image data that defines the image space, such as through automatic segmentation of the fiducial portions within the image. Also manual identification and/or combination manual-and-automatic identification may be used to determine the fiducials in the image space. The combination may include the user 72 identifying one or more pixels as seed pixels and a processor executing a segmentation program based on the seed pixels.

The identification of the fiducials in a subject space and/or navigation space occurs in block 216. The subject space may be coextensive with the navigation space and/or may overlap. Generally the navigation space is the volume that may be tracked with the tracking system, such as the localizer 88 and may encompass all or a portion of the subject or patient 30. The identification of the fiducials in the navigation space may occur in various manners such as moving a trackable instrument, such as the instrument 68, relative to the fiducial portions 120 (which may also be a tracking device) and/or the spinous process 130. The tracking system of the navigation system 26 may track the instrument 68 and the navigation system 26 may include an input to input the portions that are the fiducial portions 120 in the navigation space. The determination or identification of the position of the fiducials in the navigation space may then be used to form a translation map in block 220.

Determination of the translation map determined in block 220 may be a correlation or registration of the coordinate system of the image space to the coordinate system of the navigation space relative to and/or including the subject 30. The translation map allows for a determined position of a tracked portion in the navigation space to be translated to an equivalent or identical position in the image. Once the translated position is determined, the position may be illustrated or displayed with the display relative to the image 108, such as by the superimposing of the icon 68i on or relative to the image 108.

The image to patient registration allows for the illustration of tracked instruments or items relative to the image 108. Without the registration, however, any element not trackable or registered to the image 108 may not be appropriately or precisely illustrated at a real world position relative to the image 108. In various embodiments, therefore, the robotic coordinate system of the robot system 20 may be registered to the navigation space. Accordingly, with additional reference to FIG. 6, a robotic coordinate system or space to a navigation space registration may occur in method 224. The robotic to navigation registration may include various portions, as discussed herein.

The robotic system 20 may have a coordinate system that is determined relative to the base 34, as discussed above and further herein. Generally the robotic coordinate system may be determined relative to the subject 30, such as with a fiducial or other appropriate portion. Further the reference tracking device 54 may be used to track or determine a location relative to the navigation coordinate system of the navigation system 26. With reference to FIG. 6, the robotic coordinate system may be registered to the navigation space or navigation coordinate system according to the process 224.

In the robotic coordinate system to navigation space registration, a determination of a location of the end effector 44 relative to a base may be made in block 226. As discussed above, the determination of the position of the end effector 44 relative to the base 34 may be made in any appropriate manner. For example, various encoders may be positioned at movable joints along the robotic arm 40 of the robotic system 20. The encoders may include electrical, optical, physical and other appropriate encoders. The encoders may be used to measure and determine a relative and/or absolute movement or position of the end effector 44 relative to the base or other appropriate portion of the robotic system 20, such as the interval portion 38 of the robotic system 20. The robotic system 20 may include or be in communication with one or more processors that receive signals from the encoders to determine absolute or relative movement of portions of the robotic system 20. The processor may execute one or more instructions to determine the position of the robotic system 20, such as the end effector 44. Accordingly, the location of the end effector 44 may be determined relative to the robotic system 20 in the robotic coordinate system that may be determined relative to the base 34 or other appropriate portion of the robotic system 20.

The registration of the robotic coordinate system to the navigation space may also include a determination of the location of the base of the robotic system as within or defining the robotic coordinate system in block 228. As discussed above, the robotic coordinate system of the robotic system 20 may be determined relative to an appropriate portion, such as the subject 30, with a selected registration and fiducial portion. The robotic coordinate system, therefore, may be determined relative to or of the robotic system 20, such as relative to the base 34 or the movable portion 38 of the robotic system 20. Thus, the coordinate system of the robotic system may be determined in block 228 before registration to the navigation space that may be determined or based upon the localizer 88 or other appropriate localizer of the tracking system of the navigation system 26.

A connection of a reference device is trackable by the navigation system 26 may be made in block 230. As discussed above, the reference device 54 may be connected to the robotic system 20, such as to an immovable portion 38 thereof. The reference device 54 is fixed to the robotic system 20 at a known position, such as known within the robotic coordinate system. In various embodiments, the robotic reference 54 may be fixed at an arbitrary or non-predetermined position relative to the robotic system 20. Thus, the use of the snapshot tracker 160, as discussed herein, may be used to determine the position of the robotic reference 54 relative to the snapshot tracker that is moved by the end effector 44. The tracking system, included with the navigation system 26, may be used to track a position substantially fixed in or relative to the navigation space of the navigation system 26 with the robotic reference 54. It is understood that the reference system or device 54 may be connected to any appropriate portion and to the movable portion of the robotic system 20 is merely exemplary.

The robotic to navigation space registration may include tracking the reference frame 54 in the navigation space in block 234. A determination is then made whether the reference frame 54 is connected at a known or predetermined position relative to a selected portion of the robotic system 20, such as an immovable or removably fixed portion, such as the mount 34 or the base arm portion 38. If the robotic reference 54 is fixed at a known or predetermined portion relative to the immovable portion, such as base 38, then tracking the reference 54 with the navigation system 26 would allow for an automatic determination of the robotic coordinate system relative to the navigation space. For example, the when the robotic reference tracker 54 is tracked (e.g. sensed in the navigation space) the navigation processor 102 may access the memory system to recall the position of the robotic reference 54 in the robotic coordinate system. The determination of whether the robotic reference is at a known or predetermined position may be made in block 235 and may include a manual input to the navigation system 26, such as with the input 106, or with other appropriate determinations (e.g. a switch on the robotic system 20 where the reference frame 54 is connected).

If the determination is yes, a YES path 237 is followed. The Yes path 237 may lead to a determination of registration of the robotic coordinate system to the navigation space in block 238. The registration is based on the tracked position of the reference device 54. As the reference device 54 has a tracked position, the position is known in the navigation space. The position of the reference device 54 on the robotic system is also known. Because the position on the robotic system 20 is known of the reference device 54 and the robotic coordinates are known to the fixed or removable fixed portions (e.g. the base 38), the position of the reference device 54 in the robotic coordinate system and the navigation space are known once the reference device 54 is tracked in the navigation space. The position of the reference device 54, therefore, is used as a correlation between the robotic coordinates and the navigation space to determine a translation map and registration.

If the determination in block 235 is no, a NO path 240 is followed. The NO path 240 is followed to, in various embodiments, the snapshot tracking device 160 may then be connected to movable portion, such as the end effector 44, of the robotic system 20 in block 241. The snapshot tracking device 160 may then be tracked in block 242 in the navigation space. Thus, the reference tracking device 54 may be tracked in block 234 and the snapshot tracking device 160 may be tracked in block 242. The snapshot tracking device 160 may be tracked in a single location relative to the reference tracking device 54. The snapshot tracking device 160 may have a plurality of samples (e.g. without intentionally moving the snapshot tracking device 160) of snapshot tracking device 160 position made over a selected period of time. If a plurality of positions are determined, an average or selected number thereof may be used for the registration when using the snapshot tracking device 160.

Once the snapshot tracking device 160 is tracked in the navigation space in block 242 and the reference tracking device 54 is tracked in block 234, a determination of a correlation between the tracked position of the snapshot tracking device and the tracked position of the reference tracking device may be made in block 246. Further, the position of the end effector 44 is known in the robotic coordinate system for each tracked position in the navigation space, as the end effector is previously tracked in the robotic coordinate system (e.g. with the encoders). Based on the two tracked positions, the determined correlation allows for determination of the position of the movable portion of the robotic system 20, including the end effector 44, relative to a reference tracking device in the navigation space. The correlation of the reference tracking device 54 and the snapshot tracking device 160 relative to one another may be used to determine the position of the end effector 44 or other movable portion of the robotic system 20 relative to a stationary position in the navigation space (e.g. the space tracked by the localizer 88). Again, the position of the reference device 54 is known in the navigation space due to its being tracked in the navigation space and fixed on the robotic system 20. The reference device may be the patient tracker 58 or other appropriate reference device.

Figure 7:
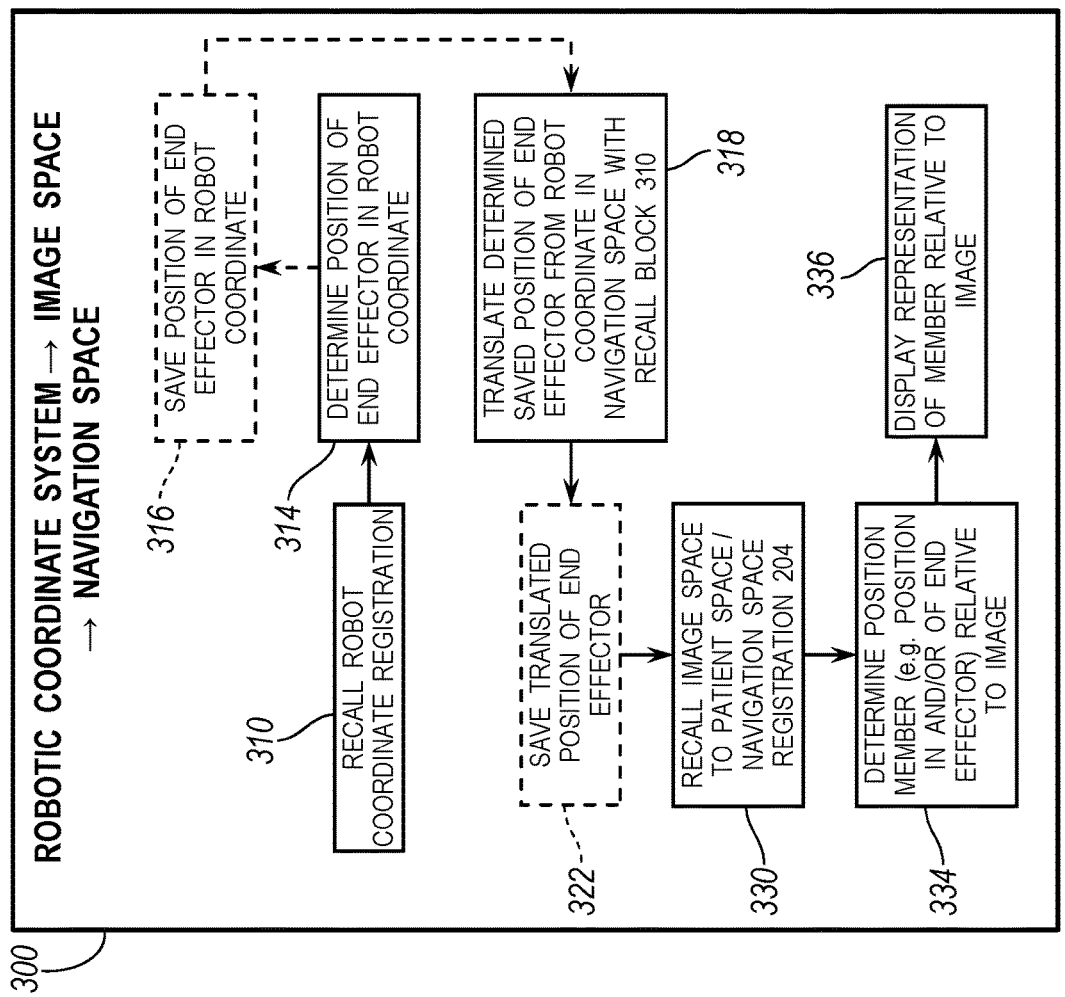
FIG. 7 is a flow chart of a method of recalling a registration for further procedure portions, according to various embodiments.

With continuing reference to FIG. 5 and FIG. 6, and additional reference to FIG. 7, the robotic system 20 having the robotic coordinate system, once registered to the navigation space, may also be used to illustrate or represent the position on the image data included in the image 108. The robotic system 20 may be used to assist the user 32 in performing a procedure relative to the subject 30. In various embodiments, the procedure may include positioning portions relative to the subject 30, such as relative to one or more vertebrae including the vertebrae 126 of the subject 30. The positioning of the selected element, such as a pedicle screw, relative to the vertebrae 126 may be performed with the robotic system 20. As discussed above, the fiducial portion 140 may be used to register the coordinate system of the robotic system 20 relative to the subject 30. Accordingly, the robotic system 20 may know or determine a position of the end effector 44 relative to the subject 30, such as the vertebrae 126 or associated vertebrae, due to the registration of the robotic system 20 relative to the subject 30. The robotic system 20, as discussed above, includes a selected tracking system such as encoders or the like.

Due to the independent nature of the navigation coordinate system and the robotic coordinate system, the position of the end effector 44 (or a member positioned within and/or through the end effector 44) relative to the subject 30 may not be known directly in the navigation coordinate system based upon the registration of the robotic system 20 relative to the subject 30. Due to the registration of the robotic system to the navigation space, as discussed in FIG. 6, and the registration of the image space to the navigation/patient space as discussed above in FIG. 5 in method 200, a position of the robotic system 20, such as the end effector 44, relative to the subject 30 may be determined relative to the image space. The two registrations may allow a third registration or determination of a position of the end effector determined with the robotic coordinate system to be made relative to the image space. It is further understood, however, that the robotic coordinate system of the robotic system 20 may be used to register to images of the subject 30, such as the image 108. As discussed above, the fiducials 140 may be used to register the robotic system to the subject 30. The images acquired of the fiducials during registration may be used to register the same images to images 108 which may also include the fiducials, such as those disclosed with the display 84. Image to image registration may include registration such as the registration discussed above and/or performed with the Mazor X™ Robotic Guidance System.

The robotic coordinate system is registered to the navigation space in the method 224, as discussed above. Accordingly, in the method 300 a recall of the robotic coordinate system registration may be made in block 310. The recall of the robotic coordinate system registration in block 310 may be a recall from a memory system, such as an intransitory memory system including any appropriate memory system. Further, the registration of the robotic coordinate system to the navigation space may be performed in substantially any appropriate time, such as during a selected procedure. Generally, the navigation system 26 may be positioned relative to the subject 30 for performing a procedure. Accordingly, the navigation space may be determined relative to the localizer, such as the localizer 88, during a selected point in a procedure and usually includes at least an area of interest of the subject 30. Recalling the registration of the robotic coordinate system to the navigation system in block 310 may be made to recall or allow for a determination of a position of the robotic system in the navigation space.

A determination of a position of the end effector 44 may be made in the robotic coordinate system in block 314. The end effector 44 may be any selected movable portion of the robotic system 20. It is understood, however, that any appropriate portion of the robotic system 20 may be a movable portion and the end effector 44 is merely exemplary. The end effector 44 may be used for assisting performing selected procedures, such as a guide for guiding the positioning of an implant into the subject 30, such as positioning a pedicle screw in the vertebrae 126. Further, as discussed above, the position of the end effector 44 may be determined in the robotic coordinate system with appropriate mechanisms such as with the encoders or the like of the robotic system 20. Thus, the position of the end effector 44 may be determined in the robotic coordinate system using the robotic system 20.

The determined position of the end effector 44 in the robotic coordinate system in block 314 may be translated to the navigation space by translating the determined position of the end effector 44 with the recalled registration from block 310 and block 318. The translation of the position of the end effector in the robotic coordinate system to the navigation coordinate system may be based upon the registration recalled in block 310 due to the robotic coordinate system to navigation space registration in the method 224.

Generally the translation may be used to determine the position of the end effector 44 in the navigation space without the navigation system 26 directly tracking the end effector 44 with the navigation system 26, such as with the localizer 88. Due to the tracked location of the end effector 44 with the robotic system 20 with the robotic coordinate system, the determined position of the end effector 44 may be determined in the navigation space due to the registration of the robotic coordinate system to the navigation coordinate system in the method 224. The translation of the robotic coordinate system to the navigation coordinate system may be made based upon the registration, such as correlating or a translation between the position (e.g. including three-dimensional location and orientation) of the end effector 44 and the robotic coordinate system to the position in the navigation coordinate system. The translation may be a mathematical translation or other appropriate translation due to the registration described above in block 224.

Once a translation is determined of the end effector 44 from the robotic coordinate system to the navigation space in block 318, an optional storing of the translated position of the end effector may be made in block 322. The saving of the translated position of the end effector in block 322 may be used for storing the translated position of the end effector 44 for various purposes, such as for portions of a procedure. As discussed above, the robotic system 20 may be used to guide a position of an implant into the subject 30, such as positioning a pedicle screw into the vertebrae 126. The positioning of the pedicle screw into the vertebrae 126 may be performed without the navigation system 26. However, the position of the robotic system 20 may be registered to the navigation system at any appropriate time, such as before placing the end effector 44 for guiding a pedicle screw. Thus, once the position of the end effector 44 is determined for performing a selected portion of a procedure, the translated position of the end effector may be made to the navigation coordinate system 26 due to the robotic coordinate system to navigation space registration in block 224. Thus, saving the translated position of the end effector in block 322 may be optional depending upon the timing of the registration of the robotic coordinate system to the navigation space in the method 224. Similarly, the saved position of the end effector and robotic coordinate system in block 316 may be optional as the position of the end effector 44 may be saved at any appropriate time and may be used to be translated to the navigation system space in block 318.

Once the translated determined/shape position of the end effector is made in block 318, a recall of the image space to patient space/navigation space from method 204 may be made in block 330. The image space to patient/navigation space registration in the method 204, as discussed above, translates the position of the navigation space to the image space. Thus, a position in the navigation space may be illustrated relative to the image 108. For example, as discussed above, in FIG. 1, the instrument may be illustrated as the icon 68*i* relative to the image 108, such as superimposed thereon, with the display device 84. Recalling of the image space to the patient space registration from block 204 may assist in determining a position of the robotic coordinate system relative to the navigation system. In particular, as discussed above, once the robotic coordinate system is registered to the navigation system, a position of the end effector 44 may be made determined in the navigation space. As the navigation space is registered to the image space in the method 204, a position of the end effector 44 may be determined relative to the image 108, even if the navigation system 26 is not directly navigating the end effector 44. Thus, recalling the image space to the patient space/navigation space registration method 204 in block 330 may be used to determine a position of the end effector relative to the image in block 334.

The determined position of the end effector 44 relative to the image in block 334 may be used to display a graphical representation 45*i* of a member 45 and or the end effector 44 relative to the image in block 346. The representation 45*i* may be of the end effector may be a direct representation of the end effector 44, a representation of an implant positioned with the end effector 44, or other appropriate representation. Regardless the determined position of the end effector relative to the image in block 334 may be displayed in block 346 as a representation, such as an icon or other appropriate graphical representation 45*i* as illustrated in FIG. 1. This allows that even if the end effector 44 is not directly navigated or tracked with the navigation system 26, the appropriate registrations and translations, as discussed above including in the method 300, may be used to illustrate a representation of a portion positioned with or relative to the end effector 44 on the image 108. This may allow the user 72, or any appropriate individual, to view a representation of a portion positioned through the end effector 44 and/or the end effector 44 relative to the subject 30 with the display 84 without directly navigating or tracking the end effector 44 with the navigation system 26.

As discussed above, the robotic coordinate system may be registered to the navigation space in the method 224 illustrated in FIG. 6. The position of the robotic system may then be displayed on an image that is registered to the navigation space according to the method 300 as illustrated in FIG. 7. It is understood, however, that the robotic coordinate system to the navigation space registration in method 224 may also be used to allow for a navigation space to be registered to the robotic coordinate system to allow for the illustration of a navigated instrument relative to the image 108, even if the navigation system is not previously registered to the image, due to the registration of the robotic coordinate system to the image space in method 182. Accordingly, with continuing reference to FIGS. 4-7 and additional reference to FIG. 8 a method 340 allows for registration of a navigation space to an image space and illustration of a tracked instrument, such as the instrument 68, on the image 108 without first performing a direct image space to subject space registration, such as the method 204.

Initially, a navigation space or coordinate system may be defined in block 342. The definition or formation of a navigation space in block 342 may include positioning a localizer relative to a selected area of interest, such as relative to the subject 30. The navigation space or coordinate system may encompass an area of interest of the subject 30, including the vertebrae 126 and/or a portion of the robotic system 20. The navigation space 342 may be defined relative to a localizer, such as the localizer 88, and/or a reference member such as the subject reference device 58. As discussed above, the image space may be registered to the navigation space in method 204. If the navigation space or subject space is not registered to the image space in method 204, however, the defined navigation space in block 342 may be used to track the snapshot tracker 160 for registration of the robotic coordinate system to the navigation space as discussed above in method 224. Thus, the robotic space or coordinate system registration to the navigation space may be performed or recalled in block 224' and allows for determination of the navigation space relative to the robotic coordinate system of the robotic system 20. As discussed above, the snapshot tracker 160 is at a known position in the robotic coordinate system due to the robotic tracking system, as discussed above. Accordingly, the snapshot tracker may be tracked in the navigation space and be used to coordinate or register the navigation space to the robotic coordinate system.

A recall and/or performing a robotic coordinate system to image space registration in method 182' may then be performed in the method 340. As discussed above the image space, such as of the image 108, may be registered relative to the robotic system 20 using the robotic fiducial images acquired in block 186. Therefore the image space may be registered to the robotic coordinate system in the method 340 by performing or recalling the registration in block 182' according to the method 182 discussed above.

With the registration of the robotic coordinate system to the navigation space in block 224' and the recall and/or performing of the robotic coordinate system to the image space in block 182', a registration of the navigation space to the image space may be performed in block 346 based upon the robotic coordinates to navigation space registration in block 224' and the robotic system to image space in block 182'. Thus, the navigation space may be registered to the image space without performing a registration directly in the navigation space to the image space as disclosed of in the method 204 in FIG. 5.

A translation of the navigation space to the image space may then occur in block 347. The translation may be a determination of the position coordinates in the navigation space to the image space due to the prior registrations in block 182' and 224'. The translation may be performed by a processor system, such as the processor system 102, to determine the relating coordinates between the navigation space and the image space.

Once the navigation space is registered to the image space in block 347 the trackable member, such as the instrument 68 with the tracking device 66, may be tracked in block 348. Tracking of the trackable member in block 348 may be with the navigation system that defines the navigation space in block 342. As discussed above, the navigation space defined by the navigation system may not be registered directly to the image space, but due to the method 340 the navigation space may be registered to the image space. Thus, a tracked member in block 348 may have a representation displayed in an appropriate location relative to the image 108 in block 350. The display of the instrument 68 may include the icon 68*i*, as illustrated in FIG. 1. In other words, a display of a representation of the instrument in block 350 may be performed by tracking the instrument in the navigation space due to the registration of the navigation space to the robotic coordinate system which has been registered to the image space, as discussed above.

As discussed above, the robotic system 20 may be used during a first portion of a procedure when navigated instruments are not being used and removed during a second portion of a procedure when navigated instruments are used.

During the second portion of the procedure, however, the user 72 may select to illustrate a position of the end effector 44 and/or an implant positioned with use of the end effector 44 even when the end effector 44 is not directly navigated and/or present in the second portion of the procedure. The translation of the determined position of the end effector 44 for the robotic coordinate system to the navigation coordinate system allows for the illustration of a representation of the end effector 44 without directly navigating and/or tracking the end effector 44.

Figure 8:
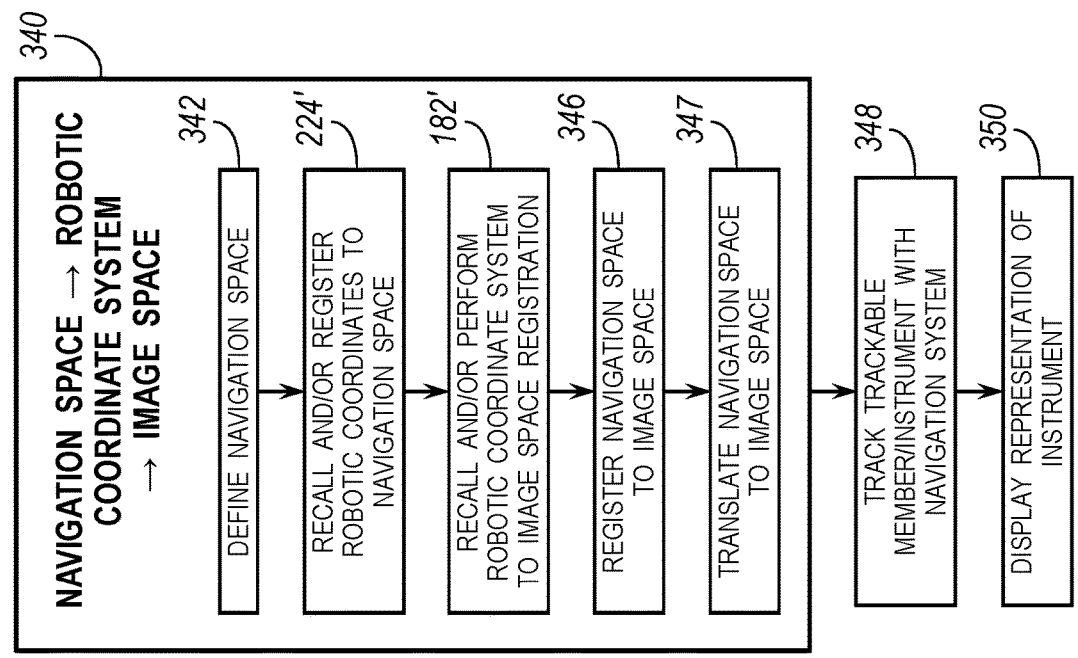
FIG. 8 is a flow chart of a method of registering a navigation space to an image space with an intermediate registration.
Figure 9:
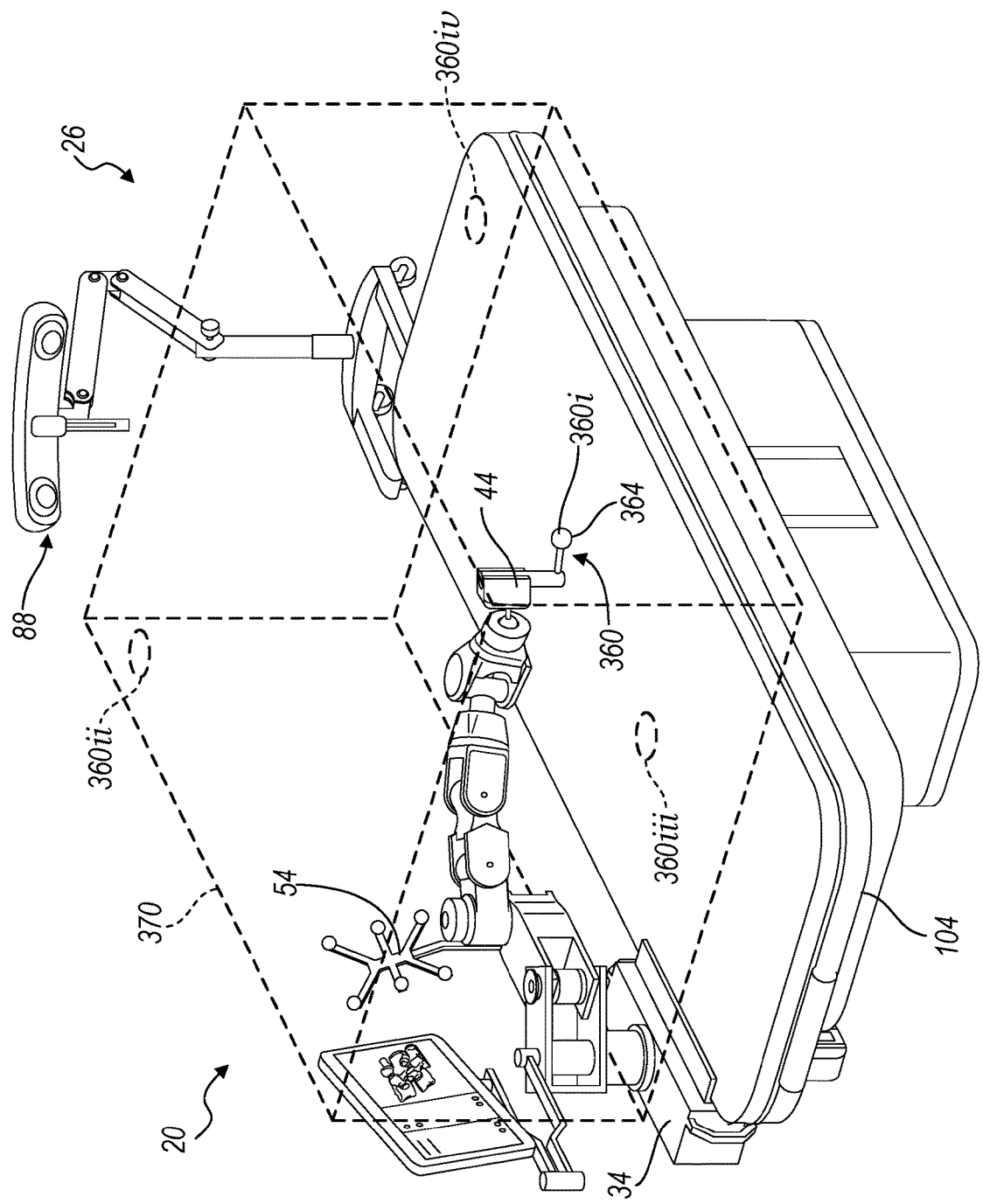
FIG. 9 is an environmental view of a dynamic reference tracking device.

With continuing reference to FIG. 2 and FIGS. 6 and 8, and additional reference to FIG. 9, the robotic system 20 may be registered to the navigation space as described above in the method 224. The robotic system 20 may be registered to the navigation space, however, with an augmentable or dynamic or movable trackable snapshot tracking sensor. The dynamic snapshot tracker 360 may include a selected tracking portion or tracking member 364. In various embodiments, the tracking member 364 may include a light reflector or light emitter that may be tracked with an optical localizer, such as the optical localizer 88. As discussed above, the snapshot tracking device 160 may be positioned relative to a navigation space such as that localized with a localizer 88.

In various embodiments, in addition to or alternatively to the single snapshot tracker 160, that may be positioned at a single position, the movable snapshot tracking device 360 may be moved in a navigation space for registration. In various embodiments, the localizer 88 may be able to define or track a tracking device in a navigation space, such as an exemplary navigation space 370. The navigation space 370 may be relative to the subject 30 and/or any other appropriate portion, such as the table 104. Generally, the navigation space 370 may be a volume that is in a room or area that may be tracked or having devices positioned therein that may be tracked with a tracking system, including the localizer 88 of the navigation system 26.

The dynamic snapshot tracking device 360 may be positioned within the volume 370 at any appropriate location such as at a first location 360*i*. As illustrated in FIG. 79 the dynamic snapshot tracking device 360 may include a single trackable member 364. The single trackable member 364 may be substantially small and allow for easy positioning in a crowded space or volume, such in a surgical operating room. For example, as illustrated in FIG. 1, an operating theater may generally have an imaging system, one or more users (e.g. surgeons, surgical nurses, technicians, etc. . . . ), and other instruments for use during a procedure. Accordingly, volume or space around the subject 30 may be at a premium and substantially tight. Therefore, including a large or obstructive snapshot tracking device may be inefficient for performing the robotic system coordinate to navigation space or coordinate registration according to the method 224.

As discussed above, the robotic system 20 includes a robotic coordinate system that may be able to determine the position of the end effector 44. The dynamic snapshot tracking device 360 may be positioned in the end effector 44 and moved within the navigation volume 370. As illustrated in FIG. 9, the dynamic snapshot tracking device 360 may be positioned at the first position 360*i*. The navigation system 26 including the localizer 88 may track the dynamic snapshot tracking device 360 including the single trackable member 364 within the navigation volume 370. The robotic system 20 may then move the dynamic snapshot tracking device 360 to other locations or positions within the navigation volume 370. For example, the robotic system 20 may move the dynamic snapshot tracking device 360 to a second position 360*ii*, a third position 360*iii*, and a fourth position 360*iv*. The dynamic snapshot tracking device 360 may be tracked at each of the four positions within the navigation volume 370. It is understood, however, that the dynamic snapshot tracking device 360 may also be moved to more or less than four positions within the navigation space 370. Regardless, the dynamic snapshot tracking device 360 may be tracked at a plurality of positions within the navigation volume, such as with the localizer 88.

By tracking the dynamic snapshot tracking device 360 at a plurality of positions within the navigation volume 370, a larger volume may be associated with positions of the dynamic snapshot tracking device 360 within the navigation space 370 rather than only positioning the dynamic snapshot tracking device 360 at a single location or position within the navigation volume 370. The exemplary four positions 360*i*-360*iv* may be used in concert to define a virtual snapshot tracking device that is larger than the single member, such as at the larger four point snapshot tracking device within the navigation volume 370. The virtual snapshot tracker may form or define an array of trackable positions larger than the tracking device 160. The larger area may lead to greater accuracy, less deviation, etc.

As the robotic system 20 is able to precisely position the dynamic snapshot tracking device 360 at the four positions within the navigation space 370 (or any appropriate number of positions within the navigation space 370), the snapshot tracking device may define a virtual snapshot tracking device that may include or define a larger volume within the navigation space 370. As the localizer 88 is used to track the dynamic tracking device 360 at each of the positions within the navigation space 370, the position of the robotic system 20, including the end effector 44 within the navigation space 370, may be more precisely determined. For example, a larger tracking device that fills more of the navigation volume 370 may be able to more precisely or accurately position or determine the position of the end effector 44 within the navigation space 370. As discussed above and with reference to the method 224, the virtual snapshot tracking device, including a plurality of positions of the snapshot tracking device 360, may then be used to register the robotic coordinate system to the navigation space coordinate system. The registration may be made based upon the known robotic coordinates of the end effector 44 at each position 360*i*-360*iv* and the tracked position at each position 360*i*-360*iv* in the navigation space. As illustrated in FIG. 9, rather than a single position of the snapshot tracking device 360 a plurality of positions may be used for the registration. The plurality of positions of the snapshot tracking device 360, however, may be coordinated to a single large snapshot tracking device that is a virtual snapshot tracking device that incorporates all of the tracked positions of the snapshot tracking device 360 within the volume 370 as exemplary illustrated as the positions 360*i*-360*iv*.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method for registering a robotic coordinate system defined by a robotic system and a navigation coordinate system defined by a tracking system localizer, comprising:
   determining a robotic coordinate system between a first portion of the robotic system and a subject separate from the first portion of the robotic system;
   determining a navigation space with a navigation coordinate system with a tracking system;
   connecting a reference marker trackable with the tracking system at a first known position relative in the robotic coordinate system relative to the first portion of the robotic system;
   determining a first reference position of the reference marker within the navigation space;
   correlating the first fixed position of the reference marker in the robotic coordinate system and the determined first reference position of the reference marker within the navigation space;
   determining a translation map between the robotic coordinate system and the navigation space based on the correlation;
   determining a registration between the robotic coordinate system and the navigation coordinate system based at least on the determined translation map;
   fixing the first portion of the robotic system in a first position;
   moving a second portion of the robotic system relative to the first portion;
   tracking a snapshot tracking device fixed relative to the second portion;
   determining a position of the snapshot tracking device in the navigation space; and
   determining a position of the second portion in the robotic coordinate system with a robotic tracking system.

2. The method of claim 1, wherein determining the position of the second portion in the robotic coordinate system with the robotic tracking system comprises:
   receiving a signal from a linkage encoder incorporated in the robotic system regarding a movement of the second portion relative to the first portion; and
   evaluating the received signal to determine the position.

3. The method of claim 2, further comprising:
   correlating the determined position of the second portion in the robotic coordinate system and the determined position of the snapshot tracking device in the navigation space.

4. The method of claim 2, further comprising:
   moving the robotic system from the first position;
   recalling the determined registration;
   correlating a prior position of at least a second portion of the robotic system in the robotic coordinate system to the navigation space based on the recalled determined registration; and
   illustrating the prior position as a graphical representation with a display device based on the correlation.

5. A system operable to register a robotic coordinate system and an image coordinate system, comprising:
   a robotic system having a robotic coordinate system defined relative to a first portion of the robotic system, wherein the robotic system is configured to be positioned relative to a subject;
   a tracking system defining a navigation space having a navigation coordinate;
   a reference marker trackable with the tracking system at a first fixed position relative in the robotic coordinate system relative to the first portion of the robotic system;
   a navigation system operable to:
      determine a first reference position of the reference marker within the navigation space;
      correlate the first fixed position of the reference marker in the robotic coordinate system and the determined first reference position of the reference marker within the navigation space;
      determine a translation map between the robotic coordinate system and the navigation space based on the correlation; and
      determine a registration between the robotic coordinate system and the navigation coordinate system based at least on the determined translation map;
   a display device configured to display a graphical representation of at least a portion moved with the robotic system based at least on the determined registration; and
   wherein the robotic system further includes:
      a second portion of the robotic system movable relative to the first portion;
      a snapshot tracking device fixed relative to the second portion;
      wherein the navigation system is further operable to determine a position of the snapshot tracking device in the navigation space; and
      wherein the robotic system includes a robotic processor operable to determine a position of the second portion in the robotic coordinate system.

6. The system of claim 5, wherein robotic system further comprises:
   a linkage encoder incorporated in the robotic system operable to generate a signal regarding a movement of the second portion relative to the first portion; and wherein the robotic processor is operable to evaluate the signal to determine the position.

7. The system of claim 6, wherein the navigation system is further operable to register an image of the subject to the navigation coordinate system;

wherein the graphical representation is superimposed on the image with the display device due at least to the determined translation map.

\* \* \* \* \*

UNITED STATES PATENT AND TRADEMARK OFFICE
CERTIFICATE OF CORRECTION

PATENT NO. : 11,135,025 B2
APPLICATION NO. : 16/244330
DATED : October 5, 2021
INVENTOR(S) : Victor D. Snyder et al.

It is certified that error appears in the above-identified patent and that said Letters Patent is hereby corrected as shown below:

In the Specification

Column 5, Line 15, delete "O-Arm®" and insert --O-arm®-- therefor

Column 5, Line 26, delete "80" and insert --30-- therefor

Column 5, Line 56, delete "imagable" and insert --imageable-- therefor

Column 5, Line 63, delete "80" and insert --30-- therefor

Column 6, Line 7, delete "92" and insert --94-- therefor

Column 6, Line 22, delete "O-Arm®" and insert --O-arm®-- therefor

Column 7, Line 1, delete "O-Arm®" and insert --O-arm®-- therefor

Column 7, Line 6, delete "reference," and insert --reference.-- therefor

Column 8, Line 61, delete "imagable" and insert --imageable-- therefor

Column 9, Line 20, delete "imagable" and insert --imageable-- therefor

Column 9, Line 24, delete "imagable" and insert --imageable-- therefor

Column 10, Line 64, delete "and or" and insert --and/or-- therefor

Column 13, Line 45, delete "34," and insert --30,-- therefor

Column 13, Line 46, delete "34" and insert --30-- therefor

Signed and Sealed this
Twenty-fourth Day of May, 2022

Katherine Kelly Vidal
*Director of the United States Patent and Trademark Office*

Column 19, Line 19, delete "and or" and insert --and/or-- therefor

Column 19, Line 20, delete "346." and insert --336.-- therefor

Column 19, Line 26, delete "346" and insert --336-- therefor